United States Patent
Clausen et al.

(10) Patent No.: US 10,117,758 B2
(45) Date of Patent: Nov. 6, 2018

(54) PROSTHETIC SPORT FEET

(71) Applicant: Össur hf, Reykjavik (IS)

(72) Inventors: Arinbjörn Viggo Clausen, Reykjavik (IS); Christophe Lecomte, Reykjavik (IS); Dana Stewart Marlin, Hafnarfjordur (IS); Lárus Gunnsteinsson, Reykjavik (IS)

(73) Assignee: Össur hf, Reykjavik (IS)

( * ) Notice: Subject to any disclaimer, the term of this patent is extended or adjusted under 35 U.S.C. 154(b) by 0 days.

(21) Appl. No.: 14/608,876

(22) Filed: Jan. 29, 2015

(65) Prior Publication Data

US 2015/0209160 A1     Jul. 30, 2015

Related U.S. Application Data

(60) Provisional application No. 61/933,190, filed on Jan. 29, 2014, provisional application No. 61/969,032, filed on Mar. 21, 2014.

(51) Int. Cl.
*A61F 2/66* (2006.01)
*A61F 2/78* (2006.01)
(Continued)

(52) U.S. Cl.
CPC .............. *A61F 2/66* (2013.01); *A61F 2/78* (2013.01); *A61F 4/00* (2013.01);
(Continued)

(58) Field of Classification Search
CPC ...... A61F 2/66; A61F 2/78; A61F 2002/6614; A61F 2002/6657
See application file for complete search history.

(56) References Cited

U.S. PATENT DOCUMENTS

| 4,938,776 A | 7/1990 | Masinter |
|---|---|---|
| 5,219,364 A | 6/1993 | Lloyd |

(Continued)

FOREIGN PATENT DOCUMENTS

| JP | 2011-182881 | 9/2011 |
|---|---|---|
| WO | WO 2013/116878 A1 | 8/2013 |

OTHER PUBLICATIONS

Cadence Concept Prosthetic Limb, http://tommytoy.typepad.com/tommy-toy-pbt-consultin/2011/09/a-concept-by-art-center-student-seth-astle-wins-the-us-portion-of-the-james-dyson-award-a-prosthetic-limb-and-bike-peda.html, published Sep. 16, 2011.

(Continued)

*Primary Examiner* — Bruce E Snow
*Assistant Examiner* — Melissa Hoban
(74) *Attorney, Agent, or Firm* — Knobbe, Martens, Olson & Bear, LLP

(57) ABSTRACT

Various features for improving the performance of prosthetic sport feet are provided. A fairing for a prosthetic sport foot can include foam components that are coupled to the foot and an elastane cover. The fairing is configured to alter the cross-sectional profile of the foot to produce a more aerodynamic shape. A prosthetic sport foot can include a hollow foot member that can be lighter weight and provide improved performance. A prosthetic sport foot can include an adjustable tension strap extending between and coupled to two portions of the foot member. A prosthetic sport foot, such as a prosthetic running foot or prosthetic cycling foot, can include an aerodynamic fairing and a cover. A prosthetic sport foot can have a varying-width profile such that a mid-section of the foot is narrower and a toe portion flares outward.

11 Claims, 14 Drawing Sheets

(51) Int. Cl.
*A61F 4/00* (2006.01)
*A61F 2/50* (2006.01)
*A61F 2/76* (2006.01)

(52) U.S. Cl.
CPC . *A61F 2002/5001* (2013.01); *A61F 2002/503* (2013.01); *A61F 2002/5009* (2013.01); *A61F 2002/5024* (2013.01); *A61F 2002/5026* (2013.01); *A61F 2002/5027* (2013.01); *A61F 2002/665* (2013.01); *A61F 2002/6614* (2013.01); *A61F 2002/6621* (2013.01); *A61F 2002/6657* (2013.01); *A61F 2002/6671* (2013.01); *A61F 2002/6678* (2013.01); *A61F 2002/7615* (2013.01)

(56) References Cited

U.S. PATENT DOCUMENTS

| | | | | |
|---|---|---|---|---|
| 5,387,246 | A * | 2/1995 | Phillips | A61F 2/602 |
| | | | | 36/117.1 |
| 6,053,946 | A | 4/2000 | Wilkinson | |
| 6,261,324 | B1 | 7/2001 | Merlette | |
| 6,406,500 | B1 | 6/2002 | Phillips | |
| 6,712,860 | B2 | 3/2004 | Rubie et al. | |
| 6,929,665 | B2 | 8/2005 | Christensen | |
| 7,503,937 | B2 | 3/2009 | Asgeirsson et al. | |
| 8,535,390 | B1 * | 9/2013 | Lecomte | A61F 2/66 |
| | | | | 623/53 |
| 8,771,372 | B1 | 7/2014 | Rubie et al. | |
| 9,668,886 | B2 * | 6/2017 | Mackiewicz | A61F 2/60 |
| 2004/0122529 | A1 * | 6/2004 | Townsend | A61F 2/60 |
| | | | | 623/52 |
| 2008/0228288 | A1 | 9/2008 | Nelson et al. | |
| 2009/0265019 | A1 * | 10/2009 | Chritstensen | A61F 2/66 |
| | | | | 623/55 |
| 2009/0299490 | A1 | 12/2009 | Summit | |
| 2010/0301632 | A1 * | 12/2010 | Bryne | A43B 5/14 |
| | | | | 296/180.1 |
| 2010/0332002 | A1 | 12/2010 | Nelson | |
| 2011/0029097 | A1 | 2/2011 | Ochoa | |
| 2013/0173023 | A1 | 7/2013 | Lecomte et al. | |
| 2013/0289741 | A1 * | 10/2013 | Halldorsson | A61F 2/80 |
| | | | | 623/34 |
| 2016/0045338 | A1 * | 2/2016 | Mackiewicz | A41B 11/14 |
| | | | | 623/33 |

OTHER PUBLICATIONS

Bespoke Innovations Prosthetics design, http://develop3d.com/reverse-engineering/dream-, published Jun. 23, 2011.

A Step Ahead Prosthetics design, http://site.mawebcenters.com/astepaheadllc/ss_lower_extremity/index.htm, http://www.astepaheadonline.com/aboutus_tech.html, websites accessed approximately Jul. 12, 2012, design available more than one year before Jan. 29, 2014.

Freedom Innovations Catapult Running Jogger (FX6) and Sprinter (FX7) products, http://www.freedom-innovations.com/catapult/, believed to have been available more than one year before Jan. 29, 2014.

May 8, 2015 International Search Report and Written Opinion for International Application No. PCT/US2015/013569 filed Jan. 29, 2015.

Partial Supplementary Search Report in corresponding European Patent Application No. 15742858.2, dated Jun. 13, 2017, in 8 pages.

* cited by examiner

PROSTHETIC SPORT FEET

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. This application claims the priority benefit of U.S. Provisional Application Nos. 61/933,190, filed Jan. 29, 2014, and 61/969,032, filed Mar. 21, 2014.

BACKGROUND

Field

The present application relates to foot prostheses in general, and more particularly, to prosthetic sport feet having aerodynamic properties.

Description of the Related Art

Various types of prosthetic foot devices are available as substitutes for human feet. Some prosthetic feet are designed especially for sporting activities such as running, both at the recreational and competitive levels. Examples of prosthetic running feet commercially available are the Össur® Flex-Run™, Össur® Flex-Sprint™, and Össur® Cheetah®. Prosthetic running feet are typically designed to efficiently store and release energy produced during running to improve performance. However, various aspects of prosthetic running feet currently available could be improved to further enhance performance. Prosthetic feet could also be improved and better optimized for other sports, such as cycling.

SUMMARY

In some embodiments, a prosthetic foot includes a prosthetic foot member extending between a proximal portion and a generally horizontal distal portion and curving concavely between the proximal portion and the distal portion. At least one portion of the foot member comprises a substantially airfoil-shaped transverse cross-section.

In some embodiments, a prosthetic foot includes a prosthetic foot member having an anterior surface and a posterior surface, extending between a proximal portion and a generally horizontal distal portion, and curving concavely lengthwise between the proximal portion and the distal portion. A surface material is disposed on at least a portion of one or both of the anterior and posterior surfaces of the foot member. The surface material provides the portion of the foot with a non-planar cross-sectional profile.

In some embodiments, surface material having a curved profile is positioned on at least a portion of the anterior surface of the foot member. The surface material positioned on the anterior surface can include at least two separate portions, with each portion spaced apart from an adjacent portion. In some such embodiments, surface material having a substantially triangular shape is positioned on at least a portion of the posterior surface of the foot member such that the prosthetic foot has a substantially air-foil shaped horizontal cross-section. Alternatively, surface material having a substantially curved profile can be positioned on at least a portion of the posterior surface of the foot member such that the prosthetic foot has a substantially elliptical horizontal cross-section. In some embodiments, a covering is positioned over the surface material. In some embodiments, the surface material is made of a foam material.

In some embodiments, a prosthetic foot includes a hollow foot element having a body surrounding a central hollow cavity, wherein at least a distal portion of the foot element includes a curved profile. The body can be made of a carbon fiber material. In some embodiments, the hollow foot element includes an opening in the body. The opening can be in fluid communication with the cavity and configured to allow for controlled release of air from the cavity during use. In some embodiments, the foot element has a planar cross-section. In other embodiments, at least a portion of the foot member includes a substantially airfoil-shaped transverse cross-section or a substantially elliptical-shaped transverse cross-section. In some embodiments, the prosthetic foot, such as a prosthetic sport foot, includes a surface material disposed on at least a portion of one or both of the anterior and posterior surfaces of the foot member. The surface material provides the portion with a non-planar cross-sectional profile.

In some embodiments, a prosthetic foot includes a plate-like foot element, wherein at least a distal portion of the foot element includes a curved profile. The prosthetic foot also includes a tension strap extending between and coupled to two locations on an anterior surface of the curved distal portion of the foot element. In some embodiments, the tension strap is adjustable. In some such embodiments, the tension strap includes a pulley and/or ratchet mechanism.

All of these embodiments are intended to be within the scope of the disclosure herein. These and other embodiments will become readily apparent to those skilled in the art from the following detailed description having reference to the attached figures, the disclosure not being limited to any particular disclosed embodiment(s).

BRIEF DESCRIPTION OF THE DRAWINGS

These and other features, aspects, and advantages of the present disclosure are described with reference to the drawings of certain embodiments, which are intended to schematically illustrate certain embodiments and not to limit the disclosure.

DETAILED DESCRIPTION

Although certain embodiments and examples are described below, those of skill in the art will appreciate that the disclosure extends beyond the specifically disclosed embodiments and/or uses and obvious modifications and equivalents thereof. Thus, it is intended that the scope of the disclosure herein disclosed should not be limited by any particular embodiments described below.

The present disclosure provides various examples of prosthetic sport feet and features for prosthetic sport feet. For example, in some embodiments, a prosthetic sport foot can be a prosthetic running foot. In other embodiments, a prosthetic sport foot can be a prosthetic cycling foot. In still other embodiments, the prosthetic sport foot can be adapted for use in other sports, or for normal use (e.g., walking). Various features as described herein can advantageously improve the aerodynamics of the sport feet to improve user performance.

Figures 1A, 1B:
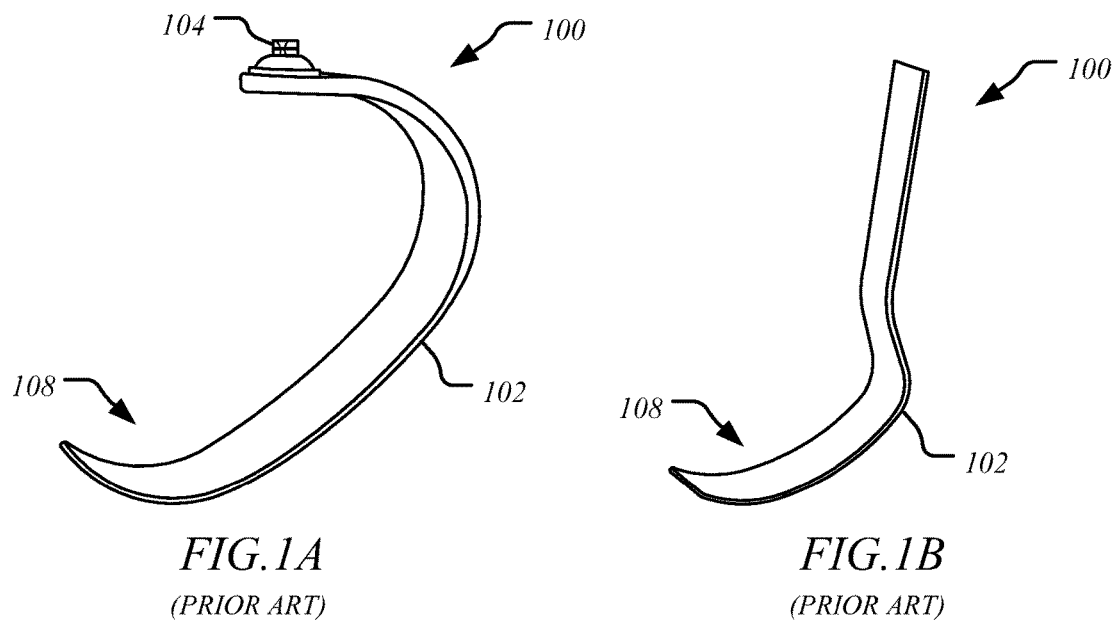
FIGS. 1A and 1B illustrate example embodiments of existing prosthetic running feet.

FIGS. 1A and 1B illustrate example embodiments of a prosthetic running foot 100. Prosthetic running feet such as those illustrated in FIGS. 1A and 1B are designed to efficiently store and release energy produced during running to improve performance. The prosthetic running foot 100 has a plate-like member 102. In some embodiments, such as the embodiment shown in FIG. 1A, the plate-like member 102 has an overall curved profile. In other embodiments, such as the embodiment shown in FIG. 1B, the plate-like member 102 has a "J" shape comprising a substantially straight and vertical proximal portion and a generally curved distal portion. A proximal portion of the plate-like member can have an attachment adapter 104 for connecting the prosthetic foot to a user's residual limb or to another prosthetic component (e.g., pylon, socket). The example prosthetic running feet shown in FIGS. 1A and 1B are the Össur® Flex-Run™ and Össur® Cheetah®, respectively; however, it will be understood by one of skill in the art that the devices described herein can also be adapted for use with other prosthetic running feet and/or with prosthetic feet other than prosthetic feet designed for running, and such variations are considered within the scope of the present disclosure. The prosthetic running feet in FIGS. 1A-1B have a monolithic member 102 made of a fiber material (e.g., carbon fiber). However, in other embodiments, the prosthetic running foot can be modular and/or made of other suitable materials.

Aerodynamic Fairing

Many factors can influence performance (e.g., speed) in sports such as running and cycling. For example, the effects of wind resistance can cost an athlete energy and time. In the field of aerodynamics, the effects of wind resistance on an object are related to the object's drag coefficient, which is a dimensionless quantity used to quantify the drag or resistance of an object in a fluid environment such as air or water. The drag coefficient depends at least in part on the profile or cross-sectional shape of the object. For example, at a given relative speed, the drag coefficient of a sprinter may be between 0.9 and 1.1, and the drag coefficient of a conventional prosthetic sport foot having a plate-like or planar cross-section, such as the foot 100 shown in FIG. 1B, may be about 1.3. An elliptical cross-sectional shape may have a drag coefficient of about 0.50, while an airfoil shape may reduce the drag coefficient to about 0.45. Therefore, changing the cross-sectional shape of a prosthetic foot from a plate to an ellipse or airfoil can reduce the drag coefficient from about 1.3 to about 0.5, which is a reduction of about 60%. Reducing the drag coefficient reduces the wind resistance on the object, which in turn can improve speed. For example, some studies have shown that reducing the wind resistance on a runner by 2% can result in a time savings of about 0.01 s in the 100 m dash to about 5.7 s in the marathon. (See, e.g., Kyle C R, Caiozzo V J, *Influence of Wind Resistance and Drag Coefficient on Performances*, 18 MED. SCI. SPORTS EXERC. 509 (1986).

FIGS. 2-7 illustrate example embodiments of an aerodynamic fairing for a prosthetic sport foot, such as the prosthetic running foot 100 shown in FIG. 1B. The fairing can advantageously regulate airflow around the foot member 102, reduce drag of the foot member 102, and/or enhance the movement of the foot member 102 through the air. In the illustrated embodiment, the fairing includes one or more anterior components 110 and a posterior component 112 disposed on the foot member 102 and a cover 114 that envelopes the foot member 102 and anterior and posterior components 110, 112.

Figure 2:
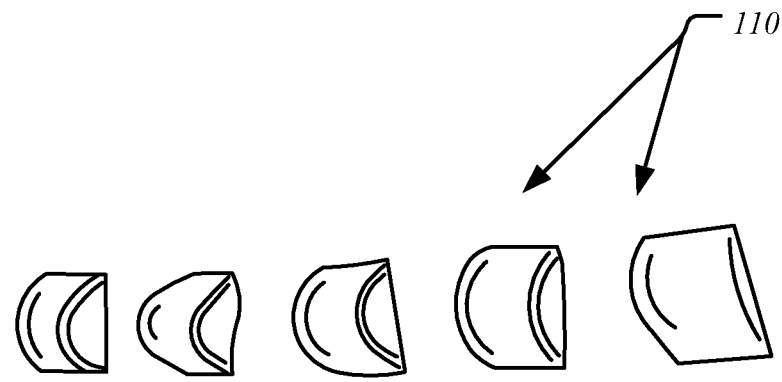
FIG. 2 illustrates an example embodiment of anterior components of an aerodynamic fairing for a prosthetic sport foot, which may be adapted for running.
Figure 3:
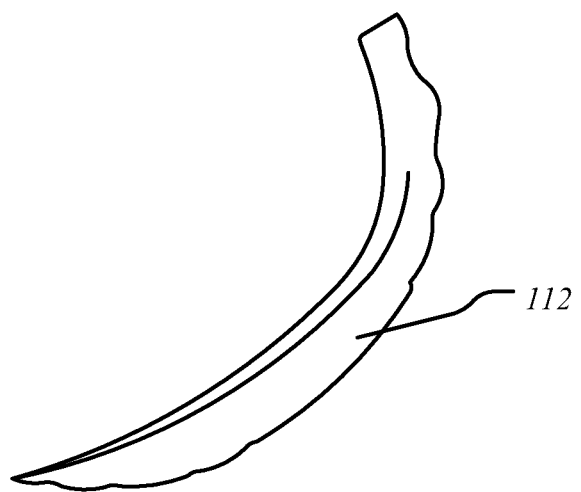
FIG. 3 illustrates an example embodiment of a posterior component of an aerodynamic fairing for a prosthetic sport foot, which may be adapted for running.
Figure 4:
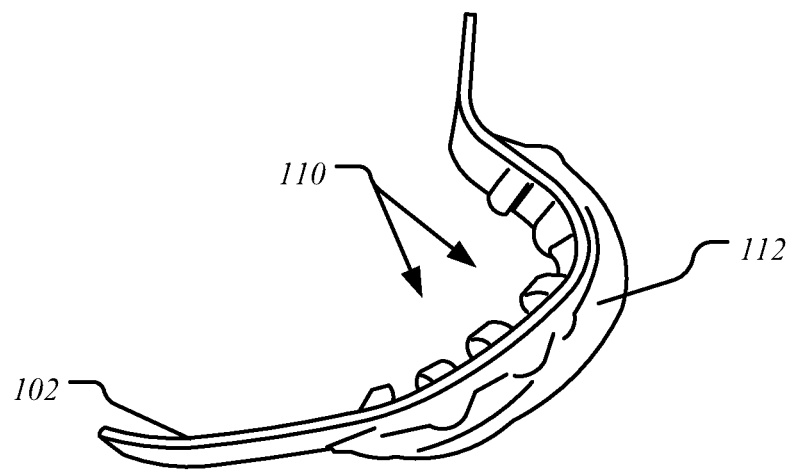
FIG. 4 illustrates the anterior and posterior fairing components of FIGS. 2 and 3 coupled to the prosthetic foot of FIG. 1B.
Figure 5:
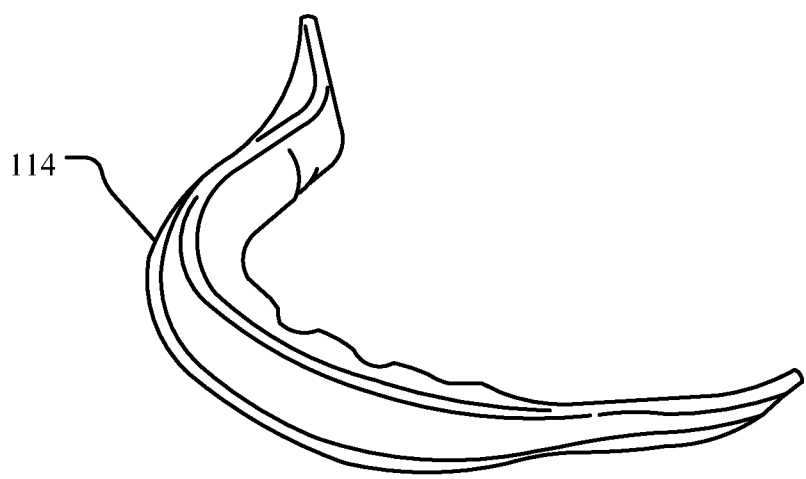
FIG. 5 illustrates the fairing and prosthetic sport foot of FIG. 4 including a cover.
Figure 6:
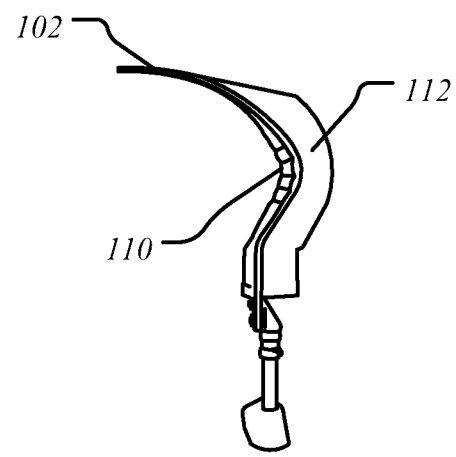
FIG. 6 illustrates another embodiment of components of an aerodynamic fairing coupled to the prosthetic sport foot.
Figure 7:
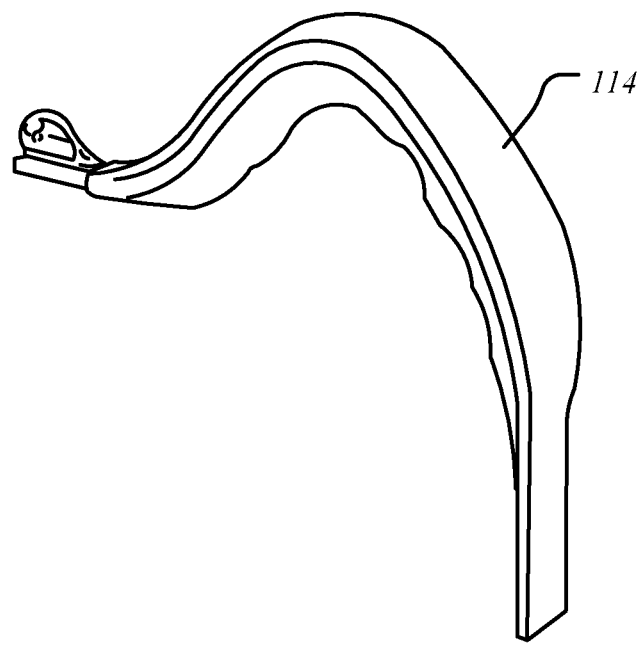
FIG. 7 illustrates the fairing and prosthetic sport foot of FIG. 6 including a cover.

As shown in FIGS. 2 and 4, the aerodynamic fairing can include a plurality of anterior components 110 disposed on, or attached to, a front surface of the curved portion of the foot member 102. The illustrated embodiment includes six anterior components 110, but more or fewer anterior components 110 are also possible. In some embodiments, the fairing includes a single, continuous anterior component 110, for example as shown in FIG. 6, which can advantageously produce a cleaner or more streamlined design, though requires a larger tool for production. In some embodiments, using multiple pieces can allow the fairing to be produced with smaller tooling. The illustrated embodiment also includes a posterior component 112 disposed on, or attached to, a rear surface of the foot member 102. In other embodiments, the fairing can include only one or more anterior components 110 or only one or more posterior components 112. In some embodiments, the fairing can include lateral and/or medial components disposed on one or both side surfaces of the foot member 102. In some embodiments, the fairing can include one or more components that extend around two or more surfaces of the foot member 102. For example, the fairing can include a component disposed around the front, rear, and both sides of the foot member 102.

In some embodiments, the anterior 110 and/or posterior 112 components are shaped to give the combined foot member 102 and fairing a generally elliptical or airfoil-shaped cross-section. For example, the one or more anterior components 110 can have a generally curved profile or shape, and the one or more posterior components 112 can have a generally triangular profile or shape to create a generally airfoil shaped cross-section or a generally curved profile or shape to create a generally elliptical cross-section. The more aerodynamic profile can advantageously reduce the drag coefficient of the foot during use, and therefore the runner, which lowers the wind resistance and can increase the runner's speed. In some embodiments, the aerodynamic profile could reduce the runner's time by hundredths or tenths of a second, for example, by about 0.01 s to about 0.2 s in a sprint race. In some embodiments, the aerodynamic profile can decrease the wind resistance or drag force by up to about 25% to about 40%.

In some embodiments, the anterior and/or posterior components 110, 112 of the fairing are made of foam. For example, the anterior and/or posterior components 110, 112 can be made of polyurethane or ethylene-vinyl acetate (EVA). A lightweight foam material can advantageously provide an aerodynamic profile with reduced added weight compared to other materials. A foam material also has a relatively low stiffness compared to the composite material of the prosthetic running foot 100 and therefore does not significantly affect the deformation characteristics of the foot. However other materials are also possible. In some embodiments, the foot member 102 itself can have the same profile as the fairing. In other embodiments, a fairing that couples to a foot member can advantageously allow for the fairing to be adjusted for different users and/or allows for the use of an existing foot member.

In the illustrated embodiments, the fairing includes a cover 114. In some embodiments, the cover 114 is made of an elastic material such as elastane (Lycra or Spandex). Other materials are also possible. The cover 114 can be stretched over the foot member 102 and anterior and/or posterior components 110, 112 after the anterior and/or posterior components 110, 112 are coupled to the foot member 102. Alternatively, the anterior and/or posterior components 110, 112 can be coupled to the inside of the cover 114, and the entire fairing assembly can be placed on the foot member 102 at one time.

The anterior and/or posterior components 110, 112 of the fairing, as well as any components disposed on the side of the foot member 102, can be coupled to the foot member 102 in a variety of ways. For example, the components can be attached to the foot member 102 with a clipping mechanism, a hook and loop type fastener (e.g., Velcro), an adhesive (e.g., epoxy or glue), magnetic strips, a sleeve (e.g., cover 114), and/or any other suitable attachment mechanism.

In some embodiments, the fairing includes one or more sensors that can measure or gather data indicative of a performance characteristic or gait information of the prosthetic foot 100, fairing, and/or user. In some such embodiments, the fairing and/or prosthetic foot 100 includes a mechanism for wirelessly transmitting data gathered by the one or more sensors (e.g., a transmitter or transceiver). The data can be transmitted to, for example, a remote computer, another device, and/or a cloud. The data can be processed on the remote computer or other device, or retrieved from the cloud and analyzed or processed. The data and/or processed data can be used by, for example, a prosthetist or the manufacturer to assist alignment, predict and prevent potential failure, evaluate potential safety hazards, analyze performance, etc. of the prosthetic foot.

Figure 14:
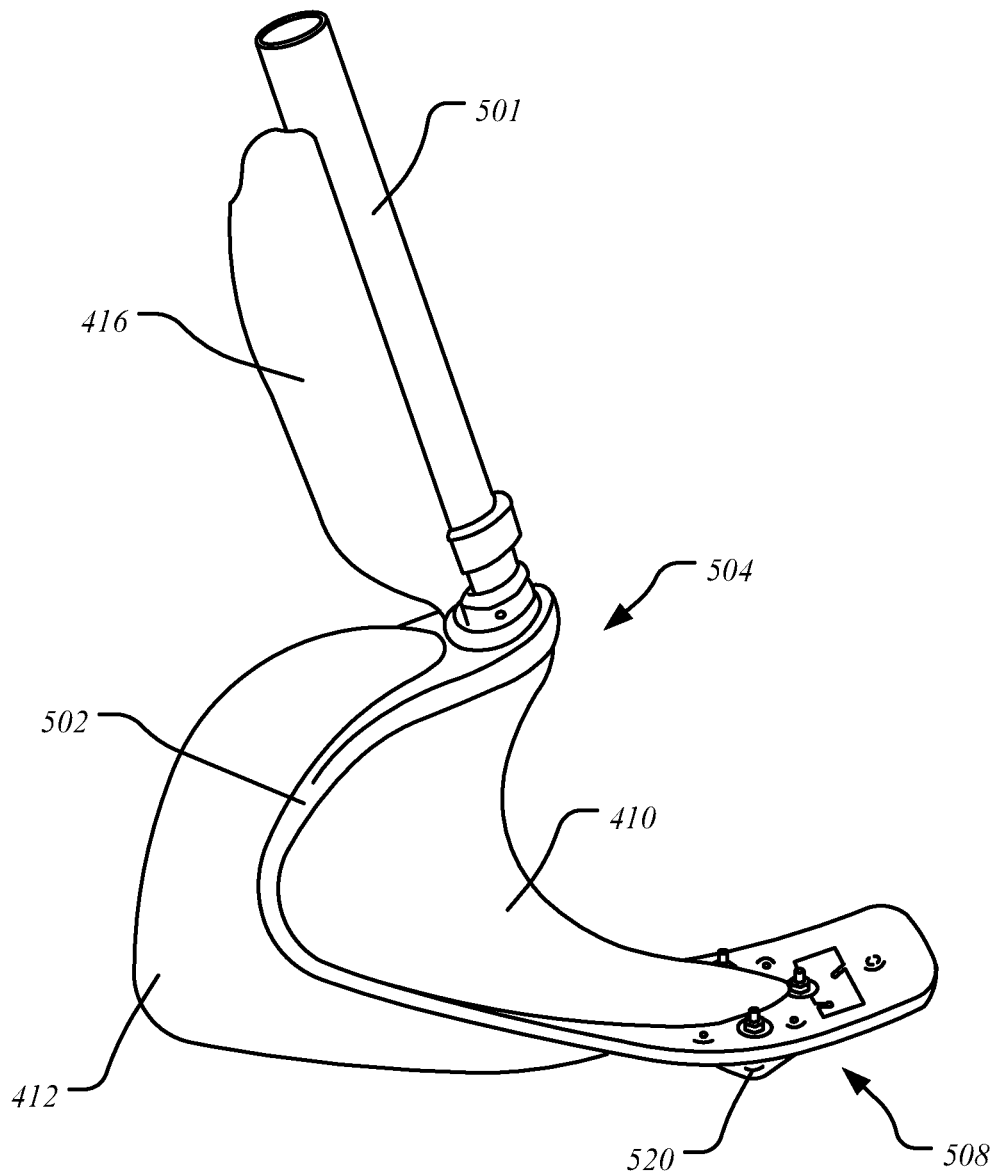
FIGS. 14-16 illustrate an example embodiment of a prosthetic sport foot, which may be adapted for cycling, including a fairing.
Figure 15:
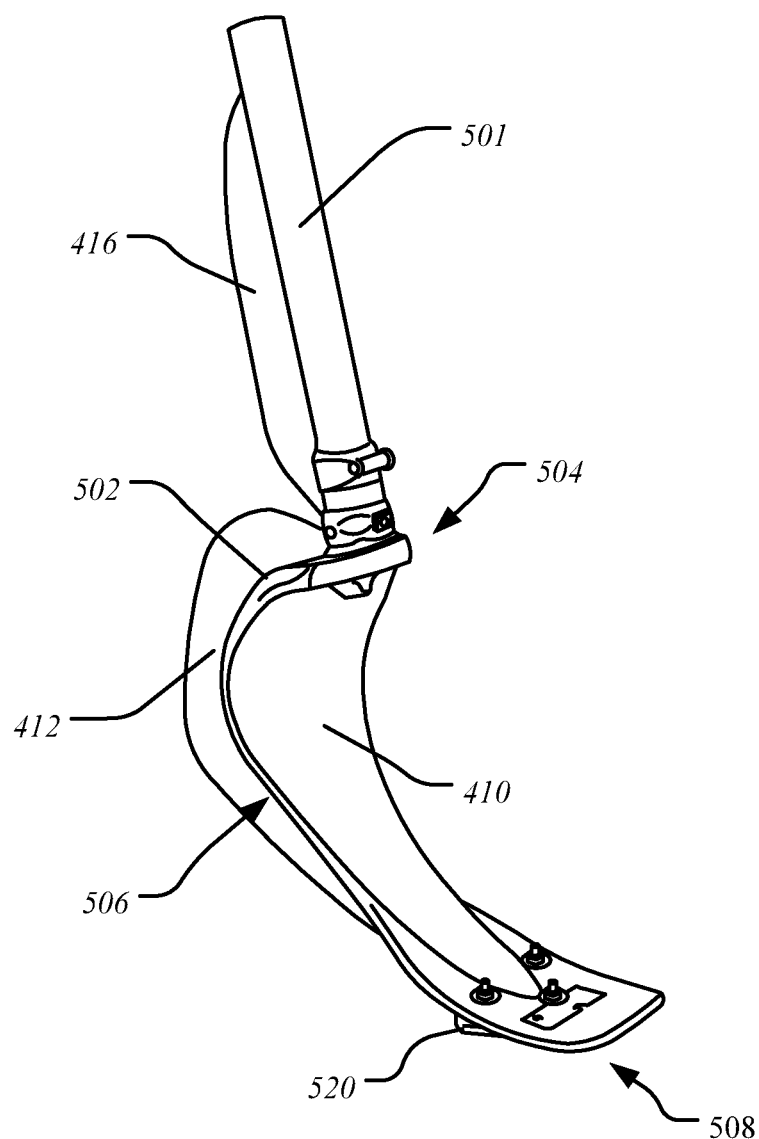
Figure 16:
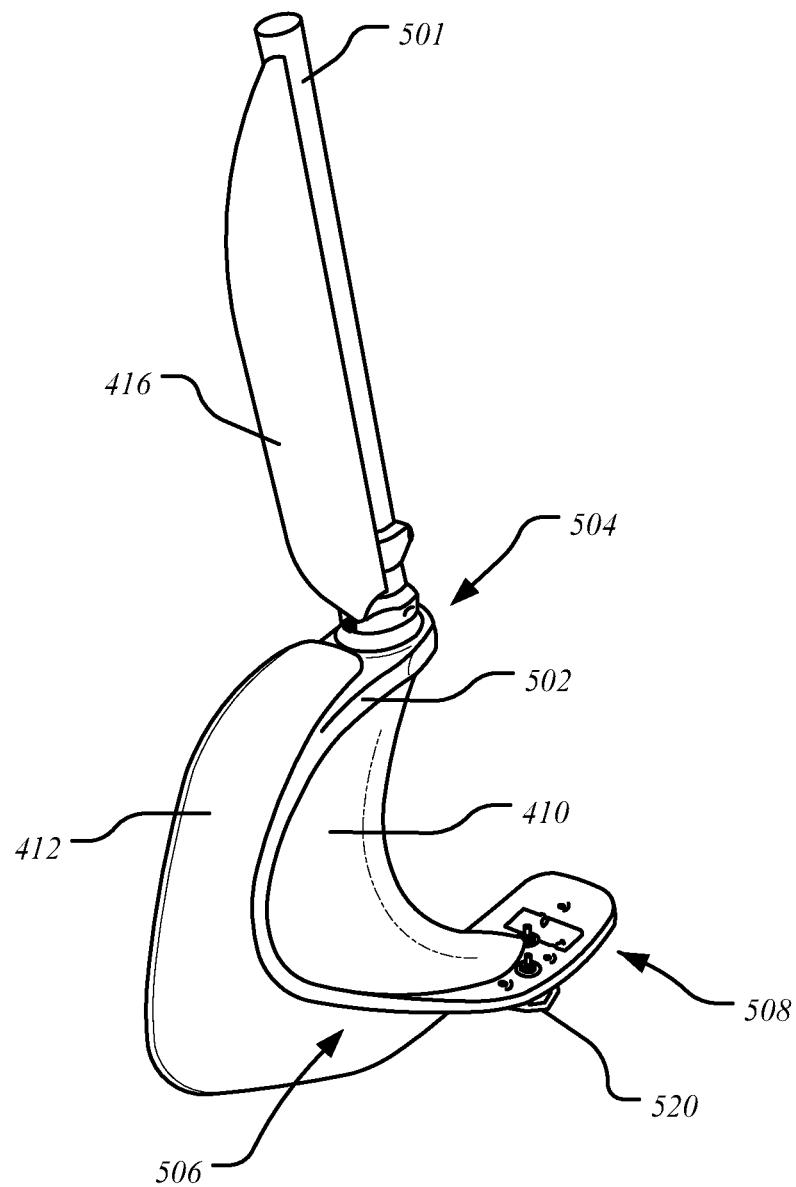

FIGS. 14-19 illustrate example embodiments of an aerodynamic fairing for a prosthetic sport foot, which may be adapted for cycling. The cycling foot can include a plate-like member 502. The plate-like member 502 can be made of one or more layers of a composite material (e.g., carbon fiber composite, glass fiber composite, carbon-glass fiber composite). The fairing can be similar to the fairing for the prosthetic running foot shown in FIGS. 2-7 and can include any or all of the same features described above in connection with the prosthetic running foot of FIGS. 2-7. As shown in FIGS. 14-16, the fairing can include an anterior component 410 disposed on, or attached to, a front surface of the foot member 502 and a posterior component 412 disposed on, or attached to, a rear surface of the foot member 502.

Figure 17:
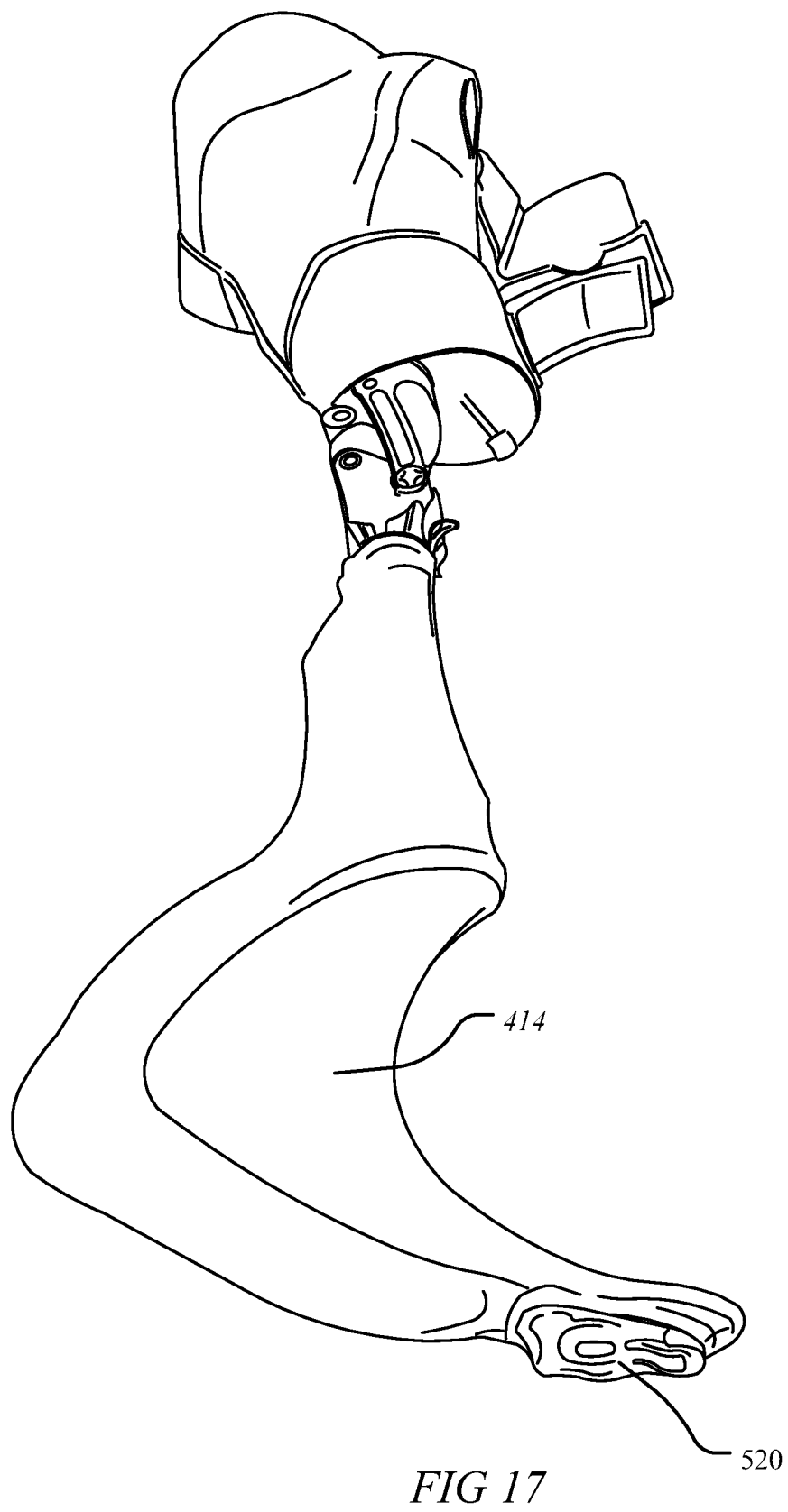
FIGS. 17-19 illustrate an example embodiment of a prosthetic sport foot, which may be adapted for cycling, including a fairing and a cover.
Figure 18:
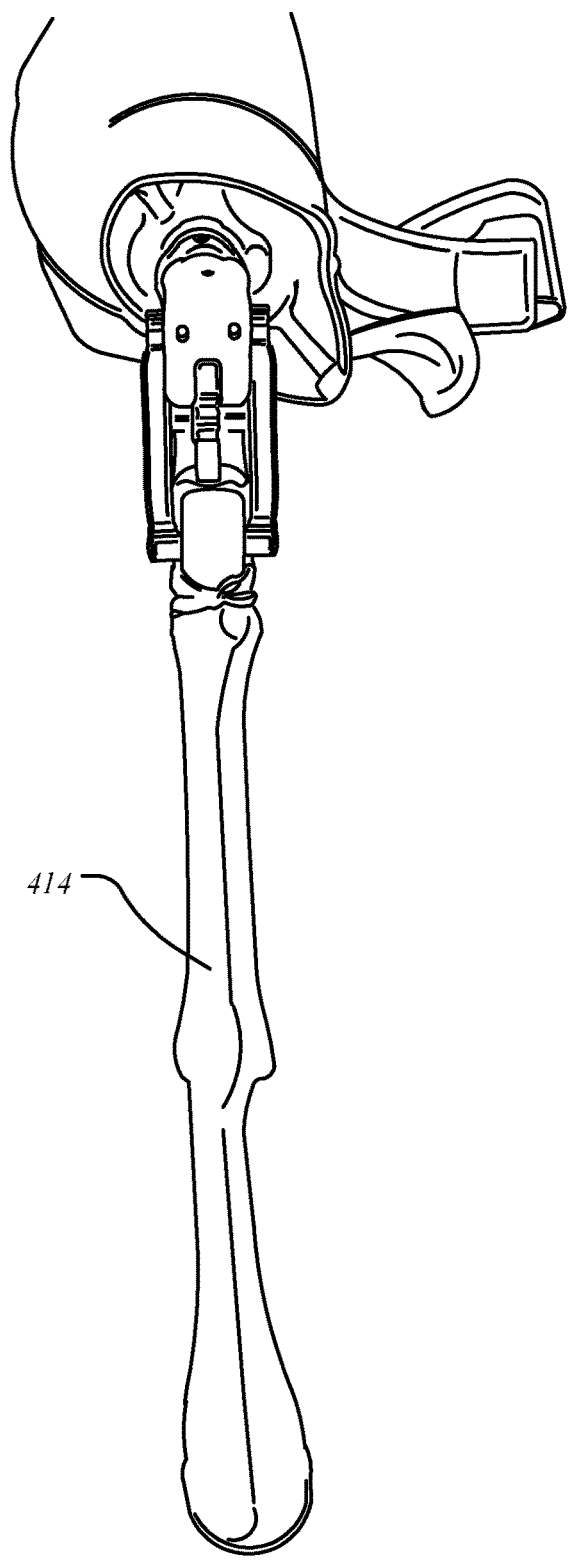
Figure 19:
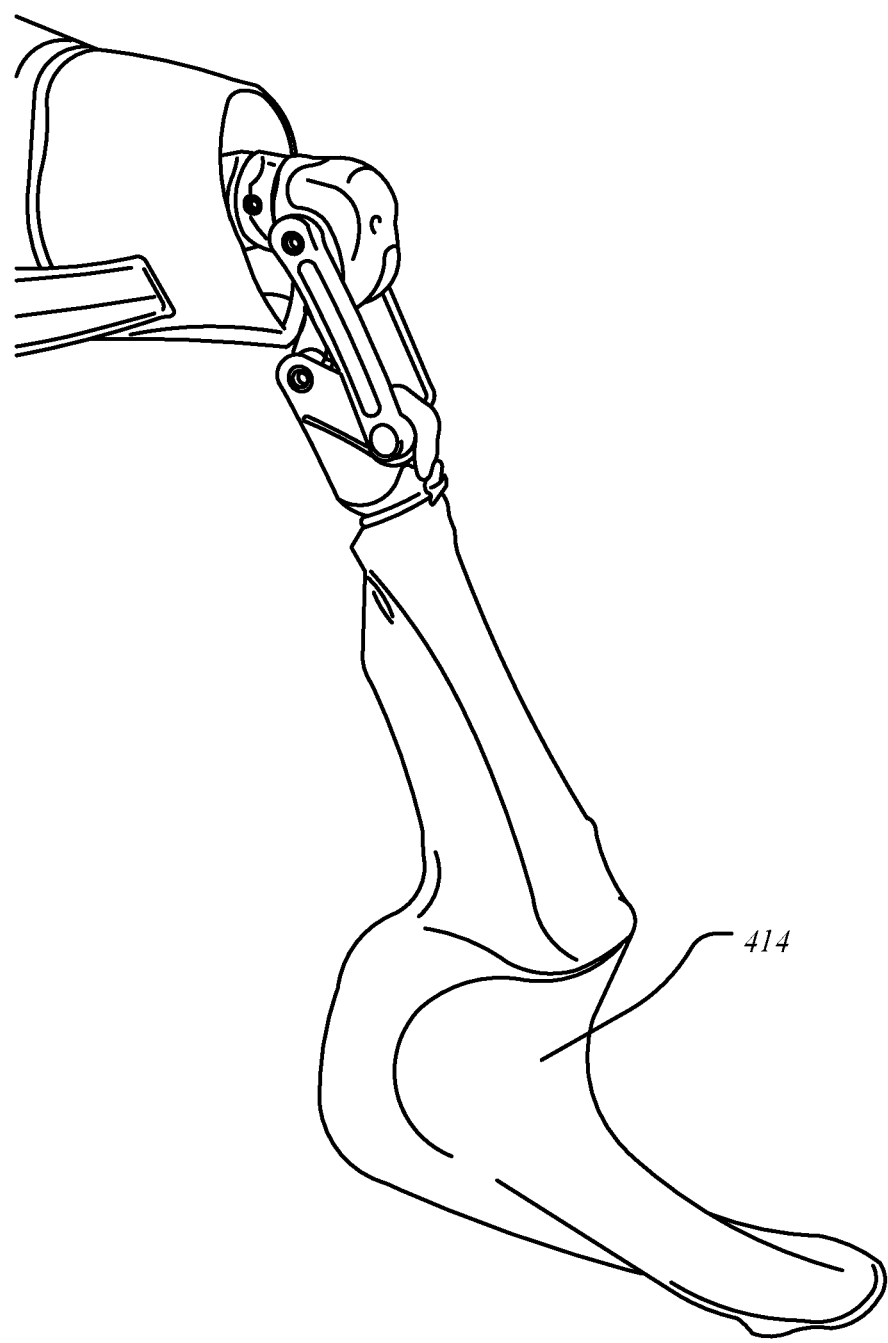

As shown, the foot member 502 can be coupled to a prosthetic pylon 501, which can be coupled to the user's residual limb or another prosthetic component (e.g., a socket, adapter, etc.). The illustrated embodiment further includes a fairing component 416 disposed on, or attached to, a rear surface of the pylon 501. The sizes, cross-sectional shapes, and other characteristics of the fairing components 410, 412, 416 can be varied as desired to achieve, for example, a desired aerodynamic profile or performance characteristic. In some embodiments, the fairing components 410, 412, 416 can have a profile or shape (e.g., curved, triangular, airfoil) that define a generally elliptical cross-section for the prosthetic sport foot, such as the cycling foot in FIGS. 14-16. In the embodiment of FIGS. 17-19, the fairing includes a cover 414, which can be similar to the cover 114 shown in FIG. 7 and described herein.

Hollow Foot Member

Figure 8:
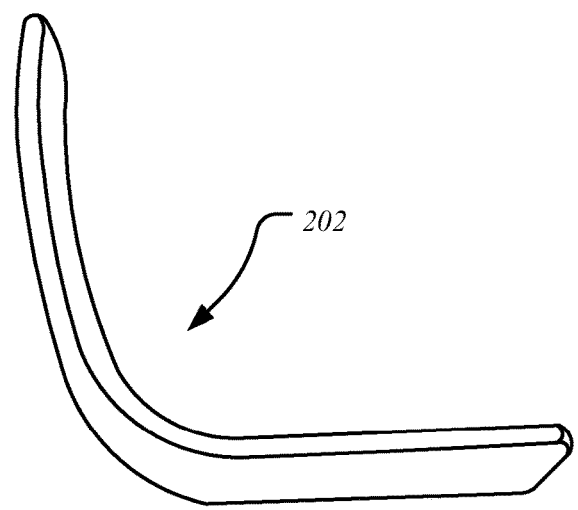
FIGS. 8 and 9 illustrate an example embodiment of a hollow prosthetic sport foot member.
Figure 9:
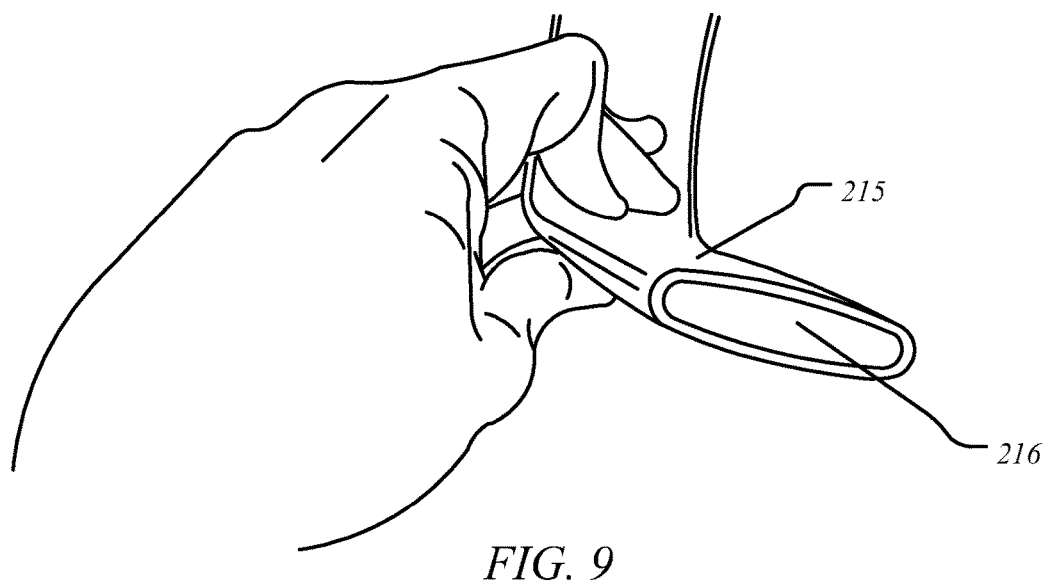

FIGS. 8 and 9 illustrate an example embodiment of a hollow foot member 202. The hollow foot member 202 has a body 215 surrounding an interior cavity or core 216. The hollow foot member 202 can advantageously have a lighter weight than conventional foot members, which can help improve running speed and/or performance. In some embodiments, the body 215 of the hollow foot member 202 is seamless. The hollow foot member 202 can be open or capped at one or both ends. Various types and configurations of caps and the degree to which the cap(s) extends into the cavity 216 can be selected to tune the flexibility and/or strength properties of the foot member 202.

In some embodiments, the foot member 202 has a symmetrical, substantially blade or oval shaped cross-section as shown in FIGS. 8 and 9. In some embodiments, an aerodynamic fairing, such as described herein and shown in FIGS. 2-7, can be coupled to the foot member 202. Alternatively, the foot member 202 can have an aerodynamic cross-section, such as an ellipse or airfoil. The cross sectional shape of the hollow foot member and internal characteristics of the foot member can be varied and selected to tune the foot, as discussed in greater detail herein. Although the hollow foot member 202 can be particularly advantageous for running feet, these features can also be incorporated into other types of prosthetic components, including foot members designed for lower activity users.

In some embodiments, a hollow foot member can have beneficial stiffness characteristics during use. The stiffness or flexibility of the hollow foot member can be tuned or adjusted by, for example, varying the cross-sectional shape of the hollow foot member. When a solid, plate-like foot member made of a carbon fiber or similar material is bent during use, the top and bottom surfaces try to deform, or compress and stretch, respectively. This deformation is resisted by the mechanical properties of the fiber, and the foot has a strong resistance to collapsing in the center. The resistance increases as the deformation or stretching and compressing forces increase, such that the stiffness of the foot increases linearly as the foot bends. In contrast, a hollow foot member having an ovular cross-sectional shape, such as the hollow foot member 202, is allowed to deform or collapse during use to compensate for the stretching and compressing forces. The top and bottom surfaces of the foot come together, decreasing the thickness of the interior cavity or core 216. This foot therefore has less resistance to bending than a solid foot, making the foot more elastic or springier. The ovular hollow foot member 202 can also exhibit non-linear deformation during use. For example, as the bending increases, the resistance to bending decreases, and as the foot is allowed to return to its resting state, the restorative energy increases in a non-linear fashion. This advantageously provides greater energy return during a toe-off portion of the gait cycle as the foot member 202 returns to its original shape. In other embodiments, if a hollow foot member is instead made with a tear-drop or circular cross-sectional shape, the foot can exhibit increased resistance to bending or flexing compared to both an ovular hollow foot member and a solid foot member.

The cavity 216 of the hollow foot member can be partially or completely filled with various materials (e.g., one or more fluids, gasses, polymers, silicones, or other media). This can allow for adjustable pressure, flexibility, weight, and/or other characteristics. For example, in one embodiment, the cavity 216 can be partially or completely filled with a gas such as helium to reduce the overall weight of the prosthetic foot. In some embodiments, the cavity 216 is separated into two or more chambers, which may or may not be fluidly connected to one another. For example, the chambers can be fluidly connected via valves that are controllable to regulate flow between chambers and/or the pressure within the chambers. Different chambers can be unfilled or can be partially or completely filled with the same or different media. The fluid or media can be disposed directly within the cavity 216 or chambers or can be housed in, for example, one or more bladders disposed within the cavity 216 or chambers.

The media within the cavity 216 or one or more chambers can be selected to have specific compressibility properties to improve performance. In some embodiments, the cavity 216 or chambers can include a media that can be used to tune certain performance characteristics (e.g., stiffness) of the foot plate. The media and/or performance characteristics can be adjusted and/or controlled in a variety of ways, for example, by the user or by a remote computer or operator. In some embodiments, the pressure of the media can be adjusted via a pump or vacuum that can increase or decrease the amount of media within the cavity 216 or one or more chambers. In some embodiments in which media is predisposed within the cavity 216 or one or more chambers, the pressure can be controlled internally with one or more valves. The media can also or alternatively be selected to have tunable properties that depend on or are affected by an external stimulus. For example, the cavity 216 or chambers can include one or more temperature responsive polymers and/or stimuli-responsive polymers. Temperature responsive polymers can be responsive to temperatures internal and/or external to the foot. For example, temperature responsive polymers may be selected to adapt to cold or heat to improve performance in various climates and temperatures. In some embodiments, a heater (e.g., electrical coil) can be disposed within the foot member 202 and selectively actuatable to change characteristics of the media by heating the media. The media can also or alternatively be responsive to electrical stimulation or an electromagnetic stimulus. For example, in some embodiments, the media is a magnetorheological fluid or elastomer that may respond to electrical stimulation or an electromagnetic stimulus by, for example, changing stiffness, thereby varying the stiffness of the foot member 202. The pump, vacuum, valves, heater (e.g., heating coil), electrical stimulator, and/or any other adjustment mechanism can be actuated manually, for example, via a knob, lever, or other adjustment device, or controlled and actuated (e.g., via an actuator) by a processor remote from the foot or a processor in or on the foot member.

In some embodiments, the cavity 216 or chambers can include one or more shock-responsive polymers. The shock-responsive polymer(s) can exhibit increased stiffness under shock load. In some embodiments, a foot including a shock-responsive polymer can be adapted for sprinting. For sprinting, it can be advantageous to have a foot that is softer or more flexible at the start of a race and then gradually stiffens during the race. For example, when the user initially applies a force to the foot, such as at the start of a race, the shock-responsive polymer(s) allows the foot to bend and provides increased springiness (e.g., energy return) at push-off. When the user strikes the foot hard against a running surface, such as during a sprint race, the shock-response polymer(s) stiffens, which increases the tension inside the foot and increases the rigidity of the foot.

In some embodiments, it can be beneficial to allow for natural and/or controlled leakage of, for example, air from the cavity 216 or chambers. For example, for distance running, it can be beneficial to the user for the cavity 216 or chambers to have a relatively high pressure or greater rigidity at the beginning of a run or race so that the foot is stiffer at the beginning of the race. Then, as the user gains speed, air or another fluid can be released from the cavity 216 or one or more chambers to increase the flexibility and/or springiness of the foot member 202. The release of fluid and pressure from the cavity 216 or chambers can be regulated with controllable valves or openings. In some embodiments, the foot can release a certain amount of air over a certain distance, for example, the distance of the particular race the user is running.

In some embodiments, one or more sensors can be placed in the cavity 216 or one or more chambers of the cavity 216. The one or more sensors can measure or gather data indicative of, for example, a performance characteristic, gait information, or environmental information, of the prosthetic foot member 202, media within the cavity 216, and/or user. In some such embodiments, the foot includes a mechanism (e.g., a transmitter or transceiver) for wirelessly transmitting data gathered by the one or more sensors. The data can be transmitted to, for example, a remote computer, another device, and/or a cloud. The data can be processed on the remote computer or other device, or retrieved from the cloud and analyzed or processed. The data and/or processed data can be used by, for example, a prosthetist or the manufacturer to assist alignment, predict and prevent potential failure, evaluate potential safety hazards, analyze performance, etc. of the prosthetic foot. In some embodiments, the data can be transmitted to a remote or on board processor, and the processor can adjust the foot or media within the cavity 216 or one or more chambers, for example, by opening or closing valves, turning a pump, vacuum, or heater (e.g., heating coil) off or on, applying electrical stimulation, etc.

Figures 10A, 10B:
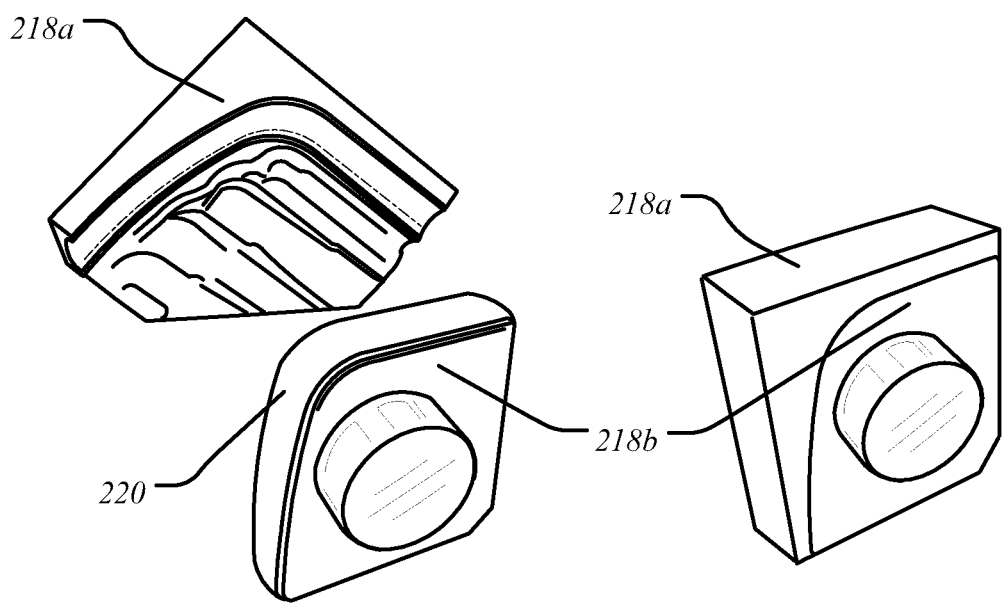
FIGS. 10A and 10B illustrate an example embodiment of a mold for manufacturing the hollow prosthetic running foot of FIGS. 8 and 9.

An example embodiment of a mold that can be used to manufacture the hollow foot member 202 is shown in FIGS. 10A and 10B. The foot member 202 can be manufactured from a tubular, woven, material, for example, a carbon glass material, that is pre-impregnated with resin, for example, epoxy resin. The tubular material can be slid over a bladder or internal core structure to establish the cavity 216. More or fewer layers of carbon fiber material can be applied at various portions of the foot member 202 to adjust the strength and stiffness as needed or desired. For example, additional layers can be used to strengthen and increase the stiffness of a particular portion of the foot member 202. In some embodiments, additional layers (for example, of carbon fiber) can be applied at locations, such as at or near an ankle region of the foot, where the foot may exhibit a greater degree of bending in use, to increase the strength in this area. Additionally, as discussed above, as the foot bends during use, the top surface of the foot will be subject to compression forces and the bottom of the foot will be subject to stretching forces. The stiffness, deformation, and/or other properties of the foot can be tuned or adjusted by using different types of cloth (e.g., fiberglass, Kevlar, Dacron, Spectra, etc.), types of weaves (e.g., woven mat, random mat, unidirectional, diagonal, etc.), numbers of layers, and/or resins (e.g., epoxy, polyester, etc.). The tube-bladder assembly 220 can then be inserted into a two-part female mold 218a, 218b. The mold is placed in an autoclave and heated under high pressure to ensure adequate resin coverage within the carbon glass weave and to cure the material. Other manufacturing techniques are also possible. For example, the foot member 202 can be produced by weaving carbon fiber around a mold while applying resin during the weaving process. Custom shapes of tubular sections can also be generated using, for example, 3-D knitting techniques.

The bladder used during manufacturing can be made of, for example, latex, nylon, or another suitable rubber tubing. The bladder can be used only for manufacturing and removed once the material has set. In some embodiments, the bladder or internal structure is made of a dissolvable material that can temporarily maintain the shape and size desired for the cavity 216 and then dissolve during or after the manufacturing process, for example, in response to a certain temperature or solvent applied to the foot member 202. Alternatively, the bladder can remain in the final product. In some embodiments, the bladder tubing can form the boundaries of the one or more chambers within the cavity 216 as discussed above. In some embodiments, a solid, honeycomb, or other type of structure can be used instead of an air, gas, or fluid filled bladder. For example, a foam material can be used to form the core of the foot member 202. A honeycomb type core can advantageously provide lightweight strength and durability. Other types and configurations of bladders and cores are also possible.

Tension Strap

Figure 11:
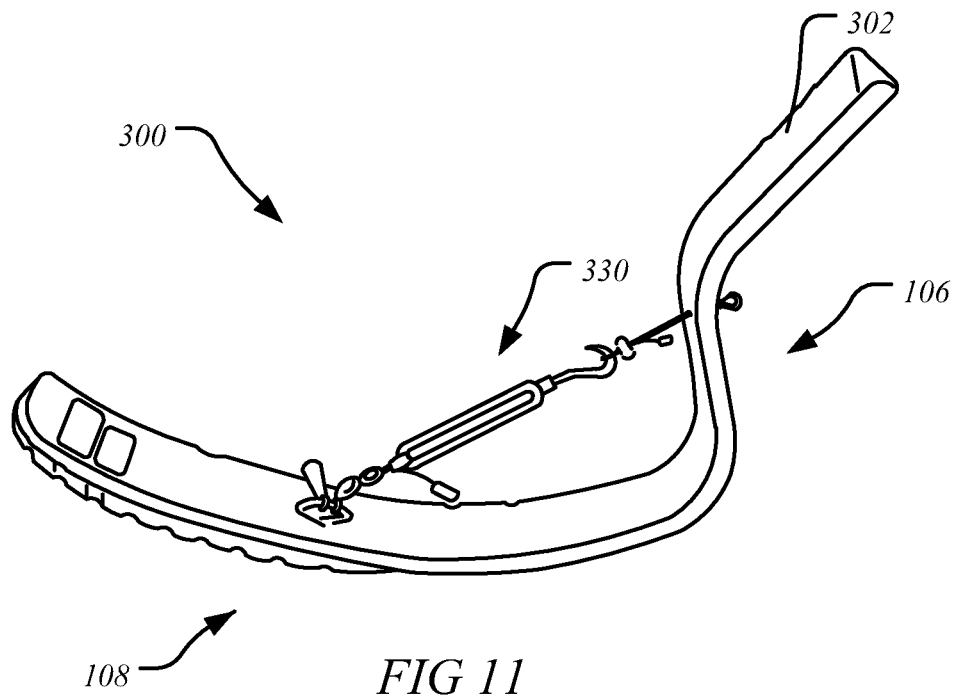
FIGS. 11 and 12 illustrate an example embodiment of a prosthetic sport foot including an adjustable tension strap.
Figure 12:
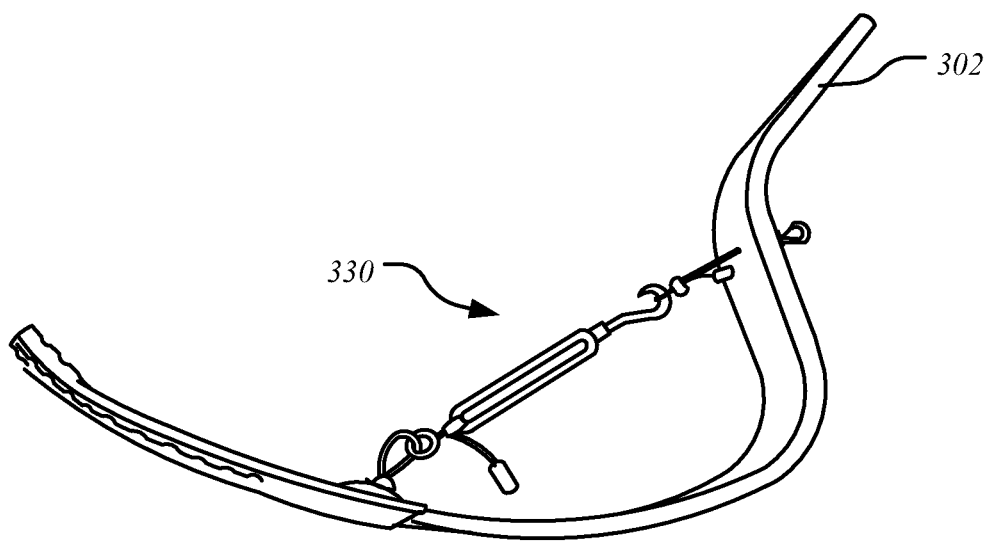
Figure 13:
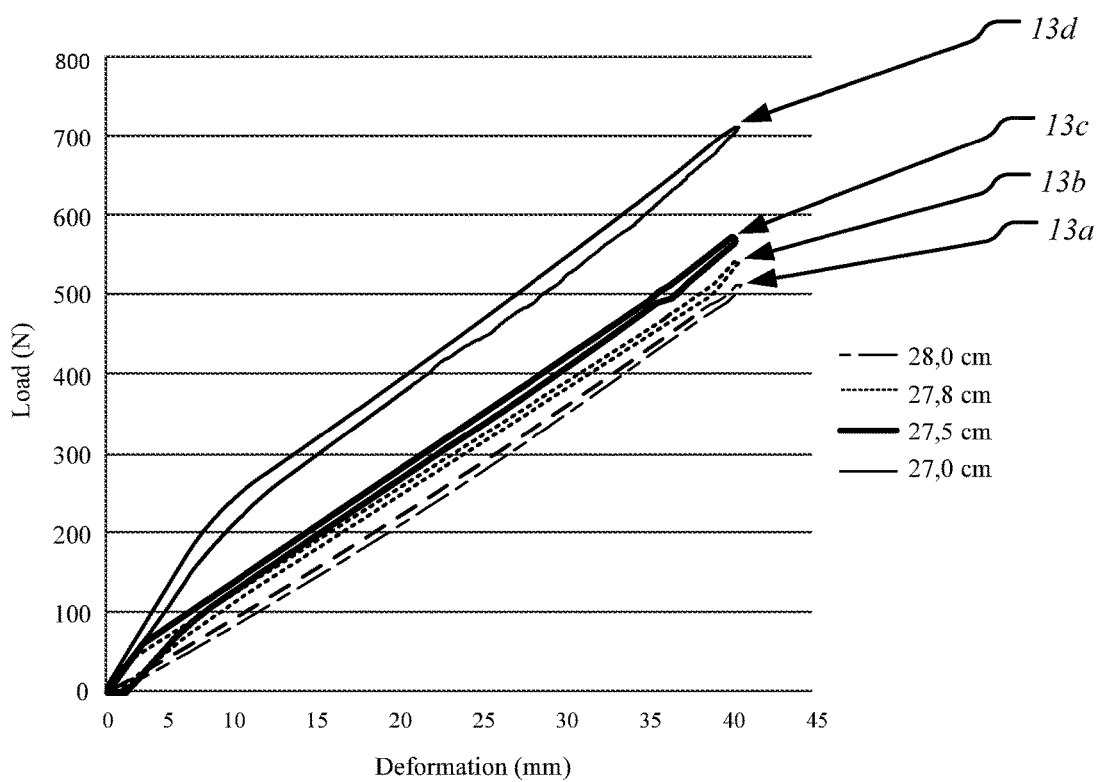
FIG. 13 illustrates a graph showing load vs. deformation for the prosthetic running foot of FIGS. 11 and 12 having varying degrees of tension on the adjustable tension strap.

FIGS. 11 and 12 illustrate an example embodiment of a prosthetic sport foot. In the illustrated embodiment, the prosthetic sport foot is a prosthetic running foot 300 that includes a tension strap 330. In the illustrated embodiment, the tension strap 330 extends between and is coupled to a lower, ground-contacting portion 108 of the foot member 302 and an upper shank portion 106 of the foot member 302. The tension strap 330 can be permanently or removably coupled to the foot member. The tension strap 330 applies tension within the curved distal portion of the illustrated foot member, which can advantageously improve performance of the foot member 302 by increasing the stiffness of the foot. For example, line 13a in the graph of FIG. 13 shows load vs. deformation data for a foot without a tension strap 330 or having no tension on the tension strap 330. Lines 13b-13d show the data for increasing tension on the tension strap 330 (e.g., by shortening the length of the tension strap 330). As shown, as the tension on the tension strap 330 increases (with line 13d showing the maximum tension of FIG. 13), the foot exhibits less deformation under a given load.

In some embodiments, the tension strap 330 is adjustable. The tension strap 330 can include various adjustment mechanisms, such as, for example, a turnbuckle screw, a ratcheting mechanism, hydraulic and/or pneumatic cylinders and/or pistons, or any other suitable adjustment mechanism. As one example, the tension strap 330 can be made of a segment of Spectra line incorporated into a pulley and ratchet control mechanism. In some embodiments, the tension strap 330 is free to compress or flex, while in other embodiments, the tension strap 330 exhibits resistance to compression. In some embodiments, the tension strap 330 has tensile resistance and controls extension or resists compression. In some embodiments, the tension strap 330 can be dynamically adjustable during use, for example, via a pre-defined program or by manual or remote control. In such an embodiment, the tension strap 330 can be tightened or loosened dynamically at certain portions of the gait cycle to enhance push-off or energy storage. The tension strap 330 can also or alternatively tighten to provide, for example, a degree of dorsiflexion during swing and released or loosened to provide enhanced plantar flexion during toe-off.

Although the illustrated embodiment includes a prosthetic running foot having a J-shape configuration as shown in FIG. 1B, a tension strap 330 can also be used with a prosthetic running foot having a shape as shown in FIG. 1A (e.g., a C-shaped foot), a hollow foot member as shown in FIGS. 8 and 9, or any other prosthetic foot. The tension strap 330 can also be used with a prosthetic running foot including an aerodynamic fairing, such as the fairings described herein and shown in FIGS. 2-7. In some embodiments, the tension strap 330 itself is shaped into an aerodynamic shape, for example, having an elliptical or airfoil cross-section.

Narrowed Mid-Foot Section

FIGS. 14-19 illustrate example embodiments of a prosthetic sport foot wherein the foot member 502 has a varying width along its length. The foot member 502 includes a proximal portion 504, a distal or toe portion 508, and a mid-section 506. The proximal portion 504 can include an adapter that can couple the foot member 502 to the pylon 501 or another prosthetic component (e.g., socket). The toe portion 508 can contact the ground or support surface in use. As shown, the mid-section 506 can be narrower (i.e., have a smaller width transverse to the longitudinal axis of the prosthetic foot when viewed from the front) than the toe portion 508. In some embodiments, the mid-section 506 is also narrower than the proximal portion 504. In other embodiments, the mid-section 506 can have the same width as the proximal portion 504. In one embodiment, the mid-section 506 can be narrower than the toe portion 508 so that the width of the foot flares outward (e.g., gradual flare) from the mid-section 506 to the toe portion 508. The narrowed mid-section 506 can advantageously reduce drag on the foot (e.g., by reducing the amount of surface area of the prosthetic foot that faces airflow during use). The narrowed mid-section 506 can also advantageously enhance springiness (e.g., reduced resistance to flexion) of the foot in use.

In some embodiments, a prosthetic sport foot having a varying width as shown can be used for cycling. There is typically less impact on the foot when cycling compared to running. The foot may therefore be able to sufficiently withstand the impact with a narrower mid-section 506. The enhanced springiness of the narrowed mid-section 506 can be particularly advantageous for cycling.

In some embodiments, a prosthetic sport foot having a varying width can be adapted for running. For example, a prosthetic running foot can benefit from a degree of resistance in the mid-section 506. A prosthetic running foot having a narrowed mid-section can be adapted to maintain the desired resistance by, for example, increasing the thickness of the material in part or all of the mid-section 506 or reinforcing the mid-section with, for example, an embedded re-bar section, one or more embedded metal or carbon rods, reinforcement via the fairing, different layup of material, use of different materials or material combinations (e.g., a hybrid composite material), or other suitable mechanisms.

As noted above, in some embodiments, the toe portion 508 is flared outward or has a greater width than the mid-section 506. This can advantageously provide greater surface area, stability, strength, and/or resistance for ground contact and impact. The greater width relative to a narrowed mid-section can also allow for an auxiliary device to be coupled or attached to the toe portion 508 more easily if desired. For example, the prosthetic feet shown in FIGS. 14-19 include a toe-clip 520 for cycling. The toe portion 508 can be sized and/or shaped to correspond to the shape of the toe-clip 520 (e.g., have generally the same width). The toe-clip 520 can engage a clipless pedal on a bicycle. In some embodiments, the toe-clip 520 can be secured to the toe portion 508 with one or more fasteners, bolts, or the like. In some embodiments, the toe-clip 520 can be removably coupled to the toe portion 508. This can advantageously allow the user to select and couple various auxiliary devices to the foot member 502 as desired for various activities or to use the foot without an auxiliary device. In another embodiment, the toe portion 508 can be sized and shaped to couple to a pedal having a toe clip. In some embodiments, the toe portion 508 can be sized, shaped, and/or adapted to receive a traction device, spikes, or another auxiliary device for running or track and field events.

With continued reference to FIGS. 14-19, the toe-clip 520 can advantageously be coupled to the toe portion 508 such that the toe-clip 520 is aligned with the pylon 501 (e.g., as opposed to being located off a centerline extending through the pylon 501). This allows the cyclist to more efficiently transfer a downward force directly onto the pedal while inhibiting generation of a moment about the pedal, thereby allowing the cyclist to more efficiently transfer pedaling force onto the bicycle via the pedals and resulting in more efficient use of energy. In contrast, able users apply a pedaling force via the front of the foot, which is offset from the axis extending through the tibia and ankle, such that a pedaling force applied by an abled cyclist may apply a moment about the pedal axis due to the offset between the ankle and the location of force transfer from the foot to the pedal.

Any of the prosthetic feet or features described herein can be used with a traction device, for example as shown and described in U.S. Pat. No. 8,535,390, which is incorporated by reference herein in its entirety and should be considered a part of this specification. Any of the feet described herein can also include spikes, for example, as may be used in track and field events. Additionally, although the concepts and features described herein have been described primarily with respect to high performance prosthetic running and cycling feet, these concepts and features can also be incorporated into other types of foot members and prosthetic components.

Although this disclosure has been described in the context of certain embodiments and examples, it will be understood by those skilled in the art that the disclosure extends beyond the specifically disclosed embodiments to other alternative embodiments and/or uses and obvious modifications and equivalents thereof. In addition, while several variations of the embodiments of the disclosure have been shown and described in detail, other modifications, which are within the scope of this disclosure, will be readily apparent to those of skill in the art. It is also contemplated that various combinations or sub-combinations of the specific features and aspects of the embodiments may be made and still fall within the scope of the disclosure. For example, features described above in connection with one embodiment can be used with a different embodiment described herein and the combination still fall within the scope of the disclosure. It should be understood that various features and aspects of the disclosed embodiments can be combined with, or substituted for, one another in order to form varying modes of the embodiments of the disclosure. Thus, it is intended that the scope of the disclosure herein should not be limited by the particular embodiments described above. Accordingly, unless otherwise stated, or unless clearly incompatible, each embodiment of this invention may comprise, additional to its essential features described herein, one or more features as described herein from each other embodiment of the invention disclosed herein.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a sub combination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A prosthetic foot comprising:
a prosthetic foot member having an anterior surface and a posterior surface, the foot member extending between a generally horizontal proximal portion and a generally horizontal distal portion, the prosthetic foot member curving rearward and downward relative to the generally horizontal proximal portion and then curving forward relative to the generally horizontal proximal portion toward the generally horizontal distal portion; and
a first surface material disposed on at least a portion of the anterior surface of the foot member and a second surface material disposed on at least a portion of the posterior surface of the foot member, wherein the first and second surface materials provide said portions with a non-planar cross-sectional profile, wherein the first and second surface materials terminate proximal to the generally horizontal distal portion,
wherein the first surface material extends along and in contact with the anterior surface of the prosthetic foot member from a horizontal bottom surface of the generally horizontal proximal portion to a horizontal top surface of the generally horizontal distal portion, the first surface material having a concave forward-facing edge,
wherein the second surface material extends along and in contact with the posterior surface of the prosthetic foot member from a horizontal top surface of the generally horizontal proximal portion to a horizontal bottom surface of the generally horizontal distal portion, the second surface material having a convex rearward-facing edge, and
wherein the first and second surface materials are configured to reduce a drag coefficient of the prosthetic foot while in use.

2. The prosthetic foot of claim 1, wherein the first surface material on the at least a portion of the anterior surface of the foot member has a substantially curved profile.

3. The prosthetic foot of claim 2, wherein the second surface material on the at least a portion of the posterior surface of the foot member has a substantially triangular shape such that the prosthetic foot has a substantially air-foil shaped horizontal cross-section.

4. The prosthetic foot of claim 2, wherein the second surface material on the at least a portion of the posterior surface of the foot member has a substantially curved profile such that the prosthetic foot has a substantially elliptical horizontal cross-section.

5. The prosthetic foot of claim 1, wherein the first and second surface materials comprise a foam material.

6. The prosthetic foot of claim 1, further comprising a pylon coupled to a proximal end of the prosthetic foot member, and a third surface material disposed on at least a portion of one or both of an anterior surface and a posterior surface of the pylon.

7. The prosthetic foot of claim 1, wherein the prosthetic foot member comprises a proximal portion, a distal toe portion and a mid-section between the proximal portion and the distal toe portion, and wherein a width of the mid-section transverse to a longitudinal axis of the prosthetic foot member is smaller than a transverse width of the distal toe portion.

8. The prosthetic foot of claim 7, wherein the width of the mid-section flares outward toward the width of the distal toe portion.

9. The prosthetic foot of claim 1, wherein the prosthetic foot member forms a widest portion of the non-planar cross-sectional profile of the prosthetic foot and the first and/or second surface materials taper forward and/or backward respectively from the prosthetic foot member.

10. The prosthetic foot of claim 9, wherein medial and lateral edges of the prosthetic foot member define a maximum medial-lateral width of the prosthetic foot.

11. The prosthetic foot of claim 1, wherein the first and second surface materials are only disposed on at least a portion of both of the anterior and posterior surfaces of the prosthetic foot member and not on side edges of the prosthetic foot member.

* * * * *